(12) United States Patent
Smith et al.

(10) Patent No.: US 7,468,116 B2
(45) Date of Patent: Dec. 23, 2008

(54) CONDUIT AND METHOD OF FORMING

(75) Inventors: Daniel John Smith, Auckland (NZ);
Nathan Lee Gray, Auckland (NZ);
Blair Victor Skelton, Pukekohe (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 547 days.

(21) Appl. No.: 11/329,747

(22) Filed: Jan. 11, 2006

(65) Prior Publication Data
US 2006/0108066 A1 May 25, 2006

Related U.S. Application Data

(62) Division of application No. 10/656,574, filed on Sep. 5, 2003, now Pat. No. 7,291,240.

(30) Foreign Application Priority Data

Sep. 9, 2002 (NZ) .................................. 521274
Sep. 11, 2002 (NZ) .................................. 521364

(51) Int. Cl.
*B32B 37/00* (2006.01)
(52) U.S. Cl. .................. 156/344; 156/184; 156/191; 156/244.13; 156/584
(58) Field of Classification Search ............... 156/184, 156/191, 244.13, 344, 584, 285, 286
See application file for complete search history.

(56) References Cited

U.S. PATENT DOCUMENTS

| 1,558,804 A | 10/1925 | Greenewald |
| 2,250,430 A | 7/1941 | Wade |
| 2,748,830 A | 6/1956 | Nash et al. |
| 3,144,313 A | 4/1966 | Pfefferle |
| 3,245,206 A | 4/1966 | Bonnet |
| 3,228,877 A | 6/1966 | Mahon |
| 3,292,346 A | 12/1966 | Adams |
| 3,294,609 A | 12/1966 | Foll |
| 3,303,105 A | 2/1967 | Konikoff et al. |
| 3,307,330 A | 3/1967 | Niedzielski et al. |
| 3,367,850 A | 2/1968 | Johnson |

(Continued)

FOREIGN PATENT DOCUMENTS

DE 198 48 172 C2 4/2000

(Continued)

OTHER PUBLICATIONS

Perma Pure Inc., One page from Perma Pure Inc. website of the product brochure #104, New PD Series Gas Dryers, at least as early as Sep. 5, 2000.

(Continued)

*Primary Examiner*—Jeff H Aftergut
(74) *Attorney, Agent, or Firm*—Trexler, Bushnell, Giangiorgi, Blackstone & Marr, Ltd.

(57) ABSTRACT

A thin ribbon spirally wound polymer conduit and method of forming, wherein a helical reinforcing bead is interposed adjacent overlapping layers of ribbon. Further, a method of continuously forming spirally wound conduit wherein a sacrificial layer, preferably having a different base polymer to that of the conduit, is first applied to the former before the conduit is formed overtop.

3 Claims, 9 Drawing Sheets

U.S. PATENT DOCUMENTS

| | | | |
|---|---|---|---|
| 3,434,471 | A | 3/1969 | Liston |
| 3,735,558 | A | 5/1973 | Skarstrom et al. |
| 3,735,559 | A | 5/1973 | Salemme |
| 3,739,815 | A | 6/1973 | Rejeski |
| 3,773,447 | A * | 11/1973 | Barratt .................. 425/86 |
| 3,834,257 | A | 9/1974 | Ganser |
| 3,856,051 | A | 12/1974 | Bain |
| 3,866,632 | A | 2/1975 | Schaffer |
| 3,889,717 | A | 6/1975 | Obadal et al. |
| 3,891,556 | A | 6/1975 | Richardson et al. |
| 3,895,630 | A | 6/1975 | Bachman |
| 3,910,808 | A | 10/1975 | Steward |
| 3,963,856 | A | 6/1976 | Carlson et al. |
| 3,966,525 | A | 6/1976 | Steward |
| 4,007,737 | A | 2/1977 | Paluch |
| 4,048,993 | A | 9/1977 | Dobritz |
| 4,204,562 | A | 5/1980 | Kelly |
| 4,207,457 | A | 6/1980 | Haglund et al. |
| 4,265,235 | A | 5/1981 | Fukunaga |
| 4,265,239 | A | 5/1981 | Fischer, Jr. et al. |
| 4,304,266 | A | 12/1981 | Kutnyak et al. |
| 4,327,775 | A | 5/1982 | Tally |
| 4,336,798 | A | 6/1982 | Beran |
| 4,337,800 | A | 7/1982 | Carlson et al. |
| 4,343,672 | A | 8/1982 | Kanao |
| 4,381,210 | A | 4/1983 | Ishizuka et al. |
| 4,420,016 | A | 12/1983 | Nichols |
| 4,456,034 | A | 6/1984 | Bixby |
| 4,462,397 | A | 7/1984 | Suzuki |
| 4,463,755 | A | 8/1984 | Suzuki |
| 4,469,495 | A | 9/1984 | Hiraizumi et al. |
| 4,488,921 | A | 12/1984 | Dougherty |
| 4,490,575 | A | 12/1984 | Kutnyak |
| 4,509,359 | A | 4/1985 | Gedeon et al. |
| 4,653,542 | A | 3/1987 | Tascher |
| 4,686,354 | A | 8/1987 | Makin |
| 4,698,890 | A | 10/1987 | Neaves |
| 4,705,543 | A | 11/1987 | Kertzman |
| 4,708,831 | A | 11/1987 | Elsworth et al. |
| 4,791,963 | A | 12/1988 | Gronert et al. |
| 4,808,201 | A | 2/1989 | Kertzman |
| 4,844,719 | A | 7/1989 | Toyomoto et al. |
| 4,875,908 | A | 10/1989 | Kikukawa et al. |
| 4,967,744 | A | 11/1990 | Chua |
| 5,042,500 | A | 8/1991 | Norlien et al. |
| 5,046,531 | A | 9/1991 | Kanao |
| 5,160,511 | A | 11/1992 | Lovelock |
| 5,233,996 | A | 8/1993 | Coleman et al. |
| 5,284,160 | A | 2/1994 | Dryden |
| 5,357,948 | A | 10/1994 | Eilentropp |
| 5,454,061 | A | 9/1995 | Carlson |
| 5,461,122 | A | 10/1995 | Yilgor et al. |
| 5,501,212 | A | 3/1996 | Psaros |
| 5,620,500 | A | 4/1997 | Fukui et al. |
| 5,637,168 | A | 6/1997 | Carlson |
| 5,640,951 | A | 6/1997 | Huddart et al. |
| 5,798,013 | A | 8/1998 | Brandenburger |
| 5,848,223 | A | 12/1998 | Carlson |
| 5,894,839 | A | 4/1999 | Rosenkoetter et al. |
| 5,975,144 | A | 11/1999 | Akedo et al. |
| 5,983,896 | A | 11/1999 | Fukunaga et al. |
| 6,024,131 | A | 2/2000 | Lester et al. |
| 6,078,730 | A | 6/2000 | Huddart et al. |
| 6,148,818 | A | 11/2000 | Pagan |
| 6,167,883 | B1 | 1/2001 | Beran et al. |
| 6,302,152 | B1 | 10/2001 | Mulligan |
| 6,367,510 | B1 | 4/2002 | Carlson |
| 6,394,145 | B1 | 5/2002 | Bailly |
| 6,432,169 | B1 | 8/2002 | Kluwe et al. |
| 6,523,538 | B1 | 2/2003 | Wikefeldt |
| 6,536,428 | B1 | 3/2003 | Smith et al. |
| 6,973,929 | B2 | 12/2005 | Gunaratnam |
| 2002/0002976 | A1 | 1/2002 | Smith et al. |
| 2002/0170940 | A1 | 11/2002 | Kazama et al. |
| 2002/0195104 | A1 | 12/2002 | Fini et al. |
| 2003/0028139 | A1 | 2/2003 | Inoue |

FOREIGN PATENT DOCUMENTS

| | | |
|---|---|---|
| EP | 0 557 040 A1 | 8/1993 |
| EP | 0 621 050 A2 | 10/1994 |
| EP | 1 153 627 A2 | 11/2001 |
| GB | 863 105 | 3/1961 |
| GB | 863 106 | 3/1961 |
| GB | 1 463 083 | 2/1977 |
| GB | 2 139 110 A | 11/1984 |
| JP | 62-236724 | 10/1987 |
| JP | 5-52378 | 3/1993 |
| JP | 2000-24111 | 1/2000 |
| WO | WO 97/18001 | 5/1997 |
| WO | WO 97/24543 | 7/1997 |

OTHER PUBLICATIONS

SympaTex, Three pages from SympaTex website, Some of the most common questions asked and some technical data on the SympaTex membrane, at least as early as Apr. 5, 2000.

Hytrel thermoplastic polyester elastomer from E.I. du Pont de Nemours and Company, 63 pages, Copyright 2000.

* cited by examiner

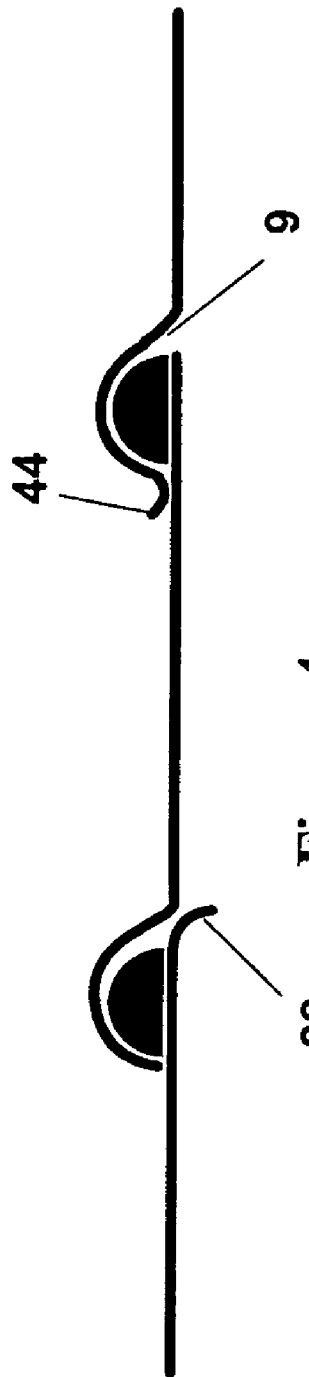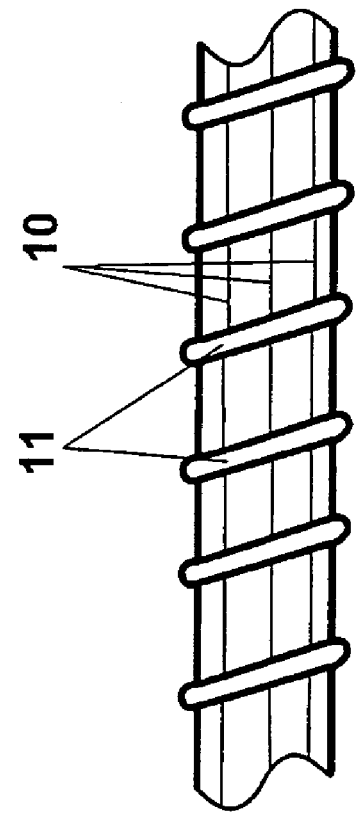

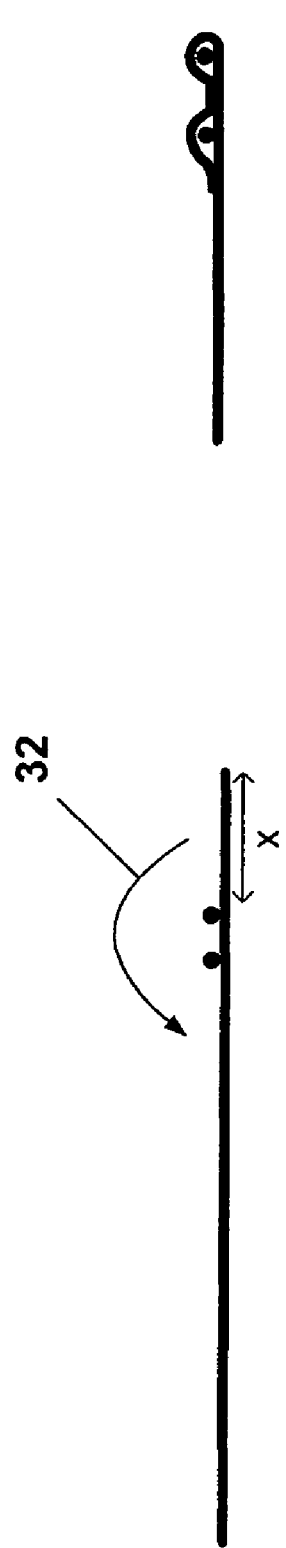
Figure 9 b
Figure 9 a
Figure 10

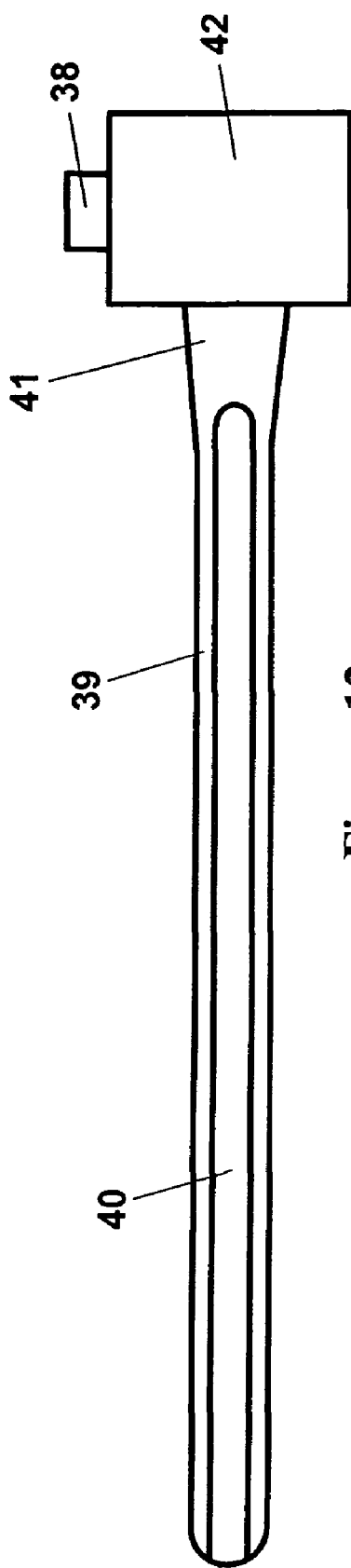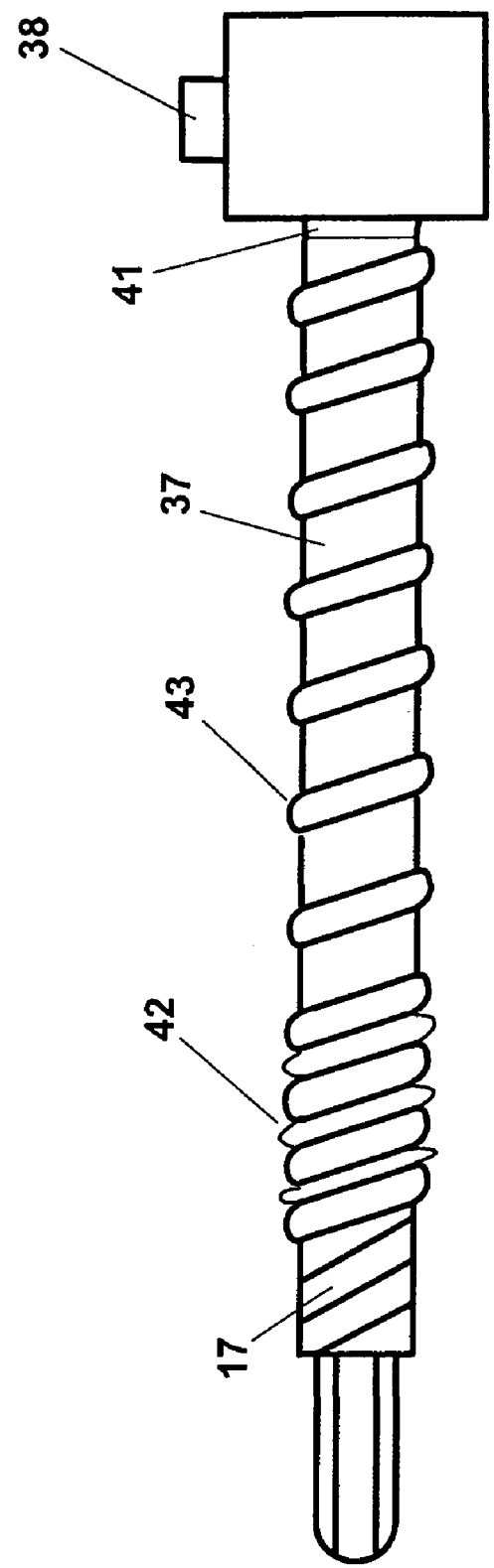
Figure 12
Figure 13

US 7,468,116 B2

CONDUIT AND METHOD OF FORMING

RELATED APPLICATION (PRIORITY CLAIM)

This patent application is a divisional of U.S. patent application Ser. No. 10/656,574, filed Sep. 5, 2003, now U.S. Pat. No. 7,291,240, and entitled "Conduit and Method of Forming", which claims priority from New Zealand Patent Application No. 521274, filed Sep. 9, 2002 and New Zealand Patent Application No. 521364, filed Sep. 11, 2002.

BACKGROUND TO THE INVENTION

1. Field of the Invention

The present invention relates to components for breathing circuits and in particular to conduits for use in the limbs of breathing circuits. The invention also relates to methods of manufacturing such conduits.

2. Summary of the Prior Art

In assisted breathing, particularly in medical applications, gases are supplied and returned through conduits. Such conduits are ideally light and flexible to achieve the highest possible level of comfort for the patient. In the prior art, thin walled conduits are known which include helical or annular reinforcing ribs which act to give the conduit better resistance to crushing and pinching, while still allowing the conduit to be light and flexible. A cross section of the wall of an example of such a conduit is shown in FIG. 1.

It is advantageous to manufacture this type of conduit as a continuous process. In the prior art this is achieved by the spiral winding of a thin polymer tape (ribbon or film) onto a former such that the edges of adjacent layers overlap a small amount. A bead of molten polymer is then applied over top the overlapping edges welding them together and simultaneously forming the helical reinforcing ribs. A disadvantage with this forming technique is the difficulty welding several adjacent layers. This problem is especially severe when multiple layer conduit walls are to be formed. While combining the application of a molten bead with another secondary thermal welding process or applying the polymer to the former as a still molten plastic does go some way to alleviating this difficulty, these solutions add complexity to the tube former and may be difficult to achieve with very thin walls.

SUMMARY OF THE INVENTION

It is an object of the present invention to provide a conduit, with particular application to the limbs of a breathing circuit, which will at least go some way towards improving on the above or which will at least provide the public and the medical profession with a useful choice, and/or to provide a method of manufacturing conduit which will at least go some way towards providing the public and manufacturers with a useful choice.

In a first aspect the invention may broadly be said to consist in a method of continuously forming conduit comprising:

continuously applying at least one thin film ribbon, each having "leading" and "trailing" lateral edges, spirally around a former rotating and advancing said conduit, with the leading edge of each turn of ribbon overlapping the trailing edge of a previous turn of ribbon on the former and the trailing edge of each turn under lapping the leading edge of a succeeding turn, while, in advance of said overlapping of said turns, applying a bead of molten plastic along the exposed trailing edge of the most recently applied turn on said former, such that a said bead is interposed between said trailing edges and said overlapping leading edges.

In a further aspect the method of continuously forming conduit may include the additional step of applying one or more heating wires to the exposed trailing edge of the ribbon prior to applying the bead, such that the bead encapsulates the one or more heating wires onto the said trailing edge.

In a further aspect the invention may broadly be said to consist in a method of continuously forming conduit wherein the former includes a plurality of rotating rods spaced about an axis and acting to support and advance the conduit during forming, further comprising:

first applying a sacrificial layer of thin plastic around said former, before said conduit is formed on said former over top of said sacrificial layer, and subsequent to forming said conduit, removing said sacrificial layer from inside said thin walled conduit after cooling.

In a further aspect the invention may broadly be said to consist in a conduit formed in accordance with a method according to any one of the preceding paragraphs.

In a still further aspect the invention may broadly be said to consist in a conduit comprising:

at least one thin plastic ribbon having a leading and a trailing lateral edge, said ribbon arranged helically with its face substantially parallel with the helix axis, and, apart from at its ends, the leading edge of each turn of ribbon overlapping the trailing edge of a previous turn, and the trailing edge of each turn of ribbon underlapping the leading edge of a succeeding turn, a plastic reinforcing bead interposed between each overlapping leading and trailing edge.

In a still further aspect the invention may broadly be said to consist in apparatus for continuously forming conduit comprising:

a former for receiving at least one thin plastic ribbon, said former drawing said ribbon around and advancing said ribbon along to procure a helical arrangement of said ribbon, the pitch of said helical arrangement being somewhat less than the width of said ribbon, means for delivering a ribbon to said former at a first position on said former, and means for continuously delivering a molten bead to said former at a second position less than one turn pitch from the position of delivery of said ribbon, said second position corresponding to an expected position of the trailing edge of a ribbon delivered by said means for delivering a ribbon.

In still a further aspect the invention may broadly be said to consist in apparatus for continuously forming conduit comprising:

a former for receiving plastic ribbon, said former drawing said ribbon around and advancing said ribbon along, to procure an overlapping helical arrangement of said ribbon, the pitch of said helical arrangement being somewhat less than the width of said ribbon, a first means for delivering a first ribbon to said former, at a first location a second means for delivering a second ribbon to said former, at a location subsequent to said first ribbon, a means for continuously delivering a molten bead to said former at a position less than one turn pitch from the position of delivery of said second ribbon said position corresponding to an expected position of the trailing edge of said second ribbon.

In a further aspect the invention may broadly be said to consist in a method for removing a releasable inner layer from within a conduit comprising:

placing said conduit, including said inner layer around an elongate shaft having a longitudinal slot, forming an adequate seal toward a first end of said shaft, effective for the conduit to at least substantially seal said slot, from the surroundings, apart from at the other end of said shaft, applying suction to said slot, initiating release of said inner layer from said conduit, removing said conduit from said shaft after said inner layer is released from said conduit.

In a further aspect the invention may broadly be said to consist in an apparatus for assisting removal of a releasable inner layer within a conduit comprising:

an elongate shaft having a longitudinal slot, a effective sealing means for making an adequate seal between said inner layer and said shaft, toward a first end of said shaft, a means to suck gases from said slot, and release said inner layer from said conduit.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIG. 4 is a cross sectional elevation of a conduit wall showing a rough inner surface resulting from the tape not completely following the contour of the molten bead.

FIG. 5 is a side elevation of a conduit according to a further embodiment of the present invention including outer axial reinforcing threads.

FIG. 9a is a cross section of a tape or ribbon illustrating the assembly of a pre-formed tape including a pair of heater wires according to a further embodiment of the present invention.

FIG. 9b is a cross section view of the pre-formed ribbon of FIG. 9a, shown assembled.

FIG. 10 is a cross section view of a conduit wall including a pair of heater wires formed from the pre-formed ribbon shown in FIG. 9b.

FIG. 12 is a plan view of an apparatus for removing the sacrificial layer.

FIG. 13 is a plan view of the apparatus of FIG. 12, shown with a conduit overtop.

DETAILED DESCRIPTION

Figure 1:
FIG. 1 is a cross sectional side elevation of a wall of a conduit according to an embodiment of the prior art.

The present invention relates to breathing conduits in general and in particular to improved methods of forming thin film (tape or ribbon) spiral wound conduits. Consequently the present invention finds application in breathing conduits fabricated from a variety of materials which may include breathable and/or non-breathable materials (breathable materials being capable of transmitting water vapour but not liquid water).

In assisted breathing, particularly in medical applications, gases having high levels of relative humidity are supplied and returned through conduits of a relatively restricted size. Build up of condensation on the inside wall of the conduit is a potential result of this high humidity. The purpose of including a breathable region or regions in the conduit wall is to allow diffusion of water vapour from the expiratory limb of the breathing circuit along the path thereof. This can reduce the build up of condensation within the expiratory limb by drying the humidified gases during their flow through the expiratory limb. This furthermore reduces the humidity of the gases arriving at ancillary equipment, such as filters, ventilators and the like, reducing the risk of condensation accumulation, thereby improving their operation, or alleviating potential detrimental effects.

The preferred breathable material is a hydrophilic polyester formed into a homogeneous flat film or ribbon. This material has been found particularly suited to thin film productions having a wall thickness of less than approximately 50 microns, and therefore find particular suitability in the manufacturing methods of the present invention. It will be appreciated that other breathable materials may also be suitable for forming breathable conduits. Such breathable materials may be breathable due to their composition, physical structure or a combination thereof.

The following embodiments will be described with particular reference to breathable thin film wall construction from materials such as those referred to above. It will be appreciated however, that in the following described embodiments the material used to form the conduit walls may be either breathable or non-breathable and may also include combinations of both breathable and non-breathable materials. It will be also appreciated for the following described embodiments that the film(s) supplied to the former may be supplied either as a preformed flat ribbon wound onto a reel or may alternatively be supplied directly to the former from an extruder. Each of these options may have associated advantages and disadvantages which will be discussed later. It will also be appreciated by those skilled in the art that the materials supplied to the former may require a number of guides tensioners and/or rollers in order to position the materials accurately and provide the necessary tension.

As a corollary of material cost it is preferred that the conduit wall be manufactured to have a relatively low wall thickness, so much so that the conduit wall membrane may be insufficiently sturdy to be self supporting. Spiral or helical reinforcing members are therefore provided as part of the tubular membrane to provide support. The helical or spiral supporting members (beads) are formed from polymer materials and may be of the same material used in the wall of the conduit or any other compatible plastics material.

Figure 2:
FIG. 2 is a cross sectional elevation of a wall of a conduit according to one embodiment of the present invention.

Referring to FIG. 1, the lay-up arrangement of a flexible breathing conduit known in the art is shown. Referring to FIG. 2, a breathing circuit limb wall cross section is shown with a thin film flexible wall. The thin film or ribbon is arranged in a spiral or helix such that the edge portions of adjacent layers overlap and form the wall of a tube. Interposed the overlapping edges of adjacent winds of ribbon, is a bead of polymer material bonded with the overlapping portions of ribbon sealing the joint between windings and forming a continuous tube. The seam is formed between the edge of a first layer of film and the edge of a second, adjacent layer of film which is laid over top of the polymer bead while the bead is molten. The overlapping layer of film because it is so thin, closely follows the contour of the bead and results in a smooth inner conduit wall. It is desirable for the ribbon to be sufficiently supple at least laterally, to conform along its overlapping portion to the contour of the bead, so that the overlapping ribbon may meet or substantially meet the underlapping ribbon at the edge of the bead.

The accompanying figures show small gaps or spaces between the reinforcing bead and the overlapping portion of ribbon. It is to be understood that these spaces are present for illustration purposes only, in order to differentiate the bead from the overlapping layer in the diagrams. In practice the overlapping layer conforms to the bead and bonds, without forming large gaps or bubbles.

Figure 3:
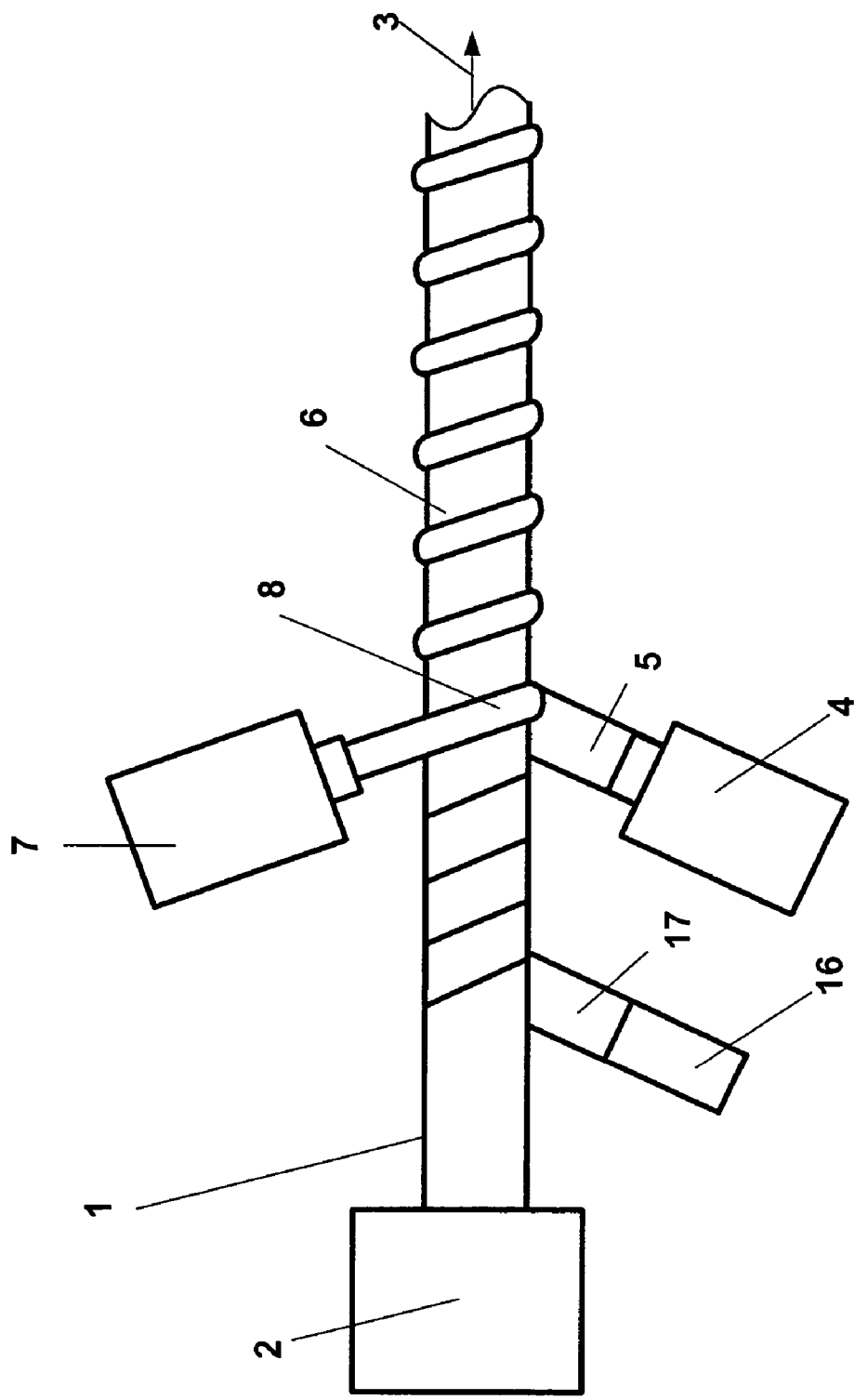
FIG. 3 is a plan view of a conduit forming device for forming a reinforced conduit according to a further embodiment of the present invention, such as the conduit pictured in FIG. 2.

An example of continuous forming apparatus suitable for manufacturing the breathing tube according to a first embodiment of the present invention described in FIG. 2 is shown in FIG. 3. The apparatus includes a former 1 preferably of a known type including a plurality of rotating rods arranged around a central support rod. The rods extend from and are rotated by a gearbox within a machine stock 2. At least in the tube forming region the rotating rods follow a helical path. The pitch angle of the rods relative to the support rod controls the pitch angle of the tube being formed. An example of such a machine is a spiral pipeline mandrel available from OLMAS SRL of Italy.

Tube being formed on the former is rotated and advanced in the direction of arrow 3 by the movement of the rotating rods. The advance speed of the former is selected relative to the rotational speed so that the pitch of the helical laying of the strip or tape on to the former 1 is a little less than the width of the strip so that adjacent turns narrowly overlap. A first extruder 4 supplies a tape or ribbon 5 of thin film polymer materials with a preferred width of approximately 10 millimetres. It will be readily understood that variation from this preferred ribbon width and size of overlap is possible in order to achieve reinforcing beads or conduits having varying pitches and/or dimensions. The ribbon 5 deposits on the former 1 in a helical fashion by action of the former. The pitch of the helical disposition of ribbon 5 is slightly less than the width of ribbon 5 and results in preferred overlap of approximately 2.5 millimetres. The helical deposition of ribbon 5 forms the wall 6 of the conduit.

An extruder 7 extrudes a bead 8 of molten or semi-molten polymer material. The molten bead 8 deposits between the overlapping portions of adjacent winds of ribbon 5 and is sufficiently heated to weld the strips of ribbon 5. In the preferred embodiment of the present invention the dimensions of the molten bead 8 are approximately 2.5 millimetres wide and 1.5 millimetres high. The conduit formed according to a preferred embodiment has an approximate internal diameter of 19 millimetres, although it will be appreciated that the methods of the present invention may be suitable for forming conduits having thin walls, irrespective of diameter of the conduit or the dimensions of the reinforcing bead.

For breathable wall conduits the thickness of the breathable film or ribbon 5 must be thick enough so that the conduit does not become too flimsy in use, but must also be thin enough so that the conduit wall is sufficiently breathable. It has been found that with polyester block copolymers, such as those described above, a wall thickness between 15 and 35 microns fulfil these requirements. The preferred wall thickness for breathable conduits according to the present invention is approximately 25 microns. A wall thickness of 25 microns has been found to provide a useful balance between breathability, flexibility and strength. The wall thickness for providing an optimal compromise of properties will ultimately depend on the specific material employed. In this regard the materials and preferred dimensions referred to in the description are illustrative and are not intended to be in any way limiting.

During the continuous manufacture of breathing conduits according to the method described above it has been found that overheating problems may occur when thin film (whether breathable or not) is used in the conduit walls. Further, the action of the helical rods rotating and advancing the conduit, may wrinkle or even damage the thin ribbon deposited on the former and may reduce the finish quality of the conduit. The mandrel temperature is raised by the continuing application of the molten bead which may also result in the thin film overheating and sticking to the mandrel or rotating rods, causing the quality of the conduit wall to suffer and/or disrupting the forming process. In order to overcome these potential problems it has been found that a sacrificial layer, wound onto the mandrel in an overlapping helix pattern before the application of the film reduces these problems and increases the quality of the conduit produced.

In order to accomplish this task the sacrificial layer of tape is significantly more rigid compared to the conduit wall and must not permanently stick to the mandrel or to the inside of the conduit wall. It has been found that a material such as bi-axially orientated polypropylene is ideally suited for the sacrificial layer. It will be appreciated that many alternative materials having a different base polymer to that of the conduit wall may also be suitable. The preferred thickness of the polypropylene sacrificial layer is between approximately 20 and 60 microns.

Referring to FIG. 3, a sacrificial layer 17 is wound from reel 16 onto the former before the breathable extruded tape 5. The heat from the applied molten bead may weld the overlapping layers of sacrificial layer to each other, but does not result in any significant bonding between the sacrificial layer and the conduit wall. Alternatively, a secondary thermal welding process may be employed to weld the overlapping layers of sacrificial tape before the conduit is formed overtop. The sacrificial layer may perform many additional advantageous functions such as those described below:

1. The dummy layer protects the helically arranged rotating rods on the mandrel from being fouled by molten plastic.
2. The sacrificial layer increases the stability of the process and may help prevent the overlapping layers that form the conduit wall from slipping and moving relative to each other.
3. The sacrificial layer provides a protective barrier between sharp edges or small protrusions on the mandrel or rotating rods, and the film or ribbon.
4. The sacrificial layer shields the thin film from the higher operating temperatures of the mandrel and reduces overheating of the film.

It will be readily appreciated by those skilled in the art that the benefits derived from the application of a sacrificial layer onto the mandrel before forming a conduit, are not limited only to material lay-up and construction wherein the helical reinforcing bead is interposed the overlapping layers.

The polypropylene layer can be easily removed from the inner wall of the finished conduit product after cooling as it does not bond significantly to the conduit. Additional means such as water cooling of the mandrel may also be provided to reduce overheating.

A method of removing a releasable inner layer (for example the sacrificial layer 17) from within a length of conduit 37, subsequent to forming the conduit, will be described with reference to FIGS. 12 and 13. A shaft 39 is provided having a substantially hollow cylindrical shape of a length longer than that of the desired conduit product length. The shaft 39 has a longitudinal slot 40 and is cantilevered from stock 42. The slot of shaft 39 is in fluid connection with a suction or vacuum source 38 via stock 42.

The outer diameter of the shaft is preferably smaller than that of the conduit 37. A tapered shoulder region 41 is provided at the built-in end of the shaft 39 in order to enable an effective seal to be formed between the inner layer and the shoulder portion when suction is applied. Alternatively, the seal may be formed between the shaft and the outside of the conduit. The effect is to seal (so far as necessary) at least the inside of the releasable inner layer from the surroundings.

In use, and in order to remove the sacrificial layer 17 from the inner wall of the conduit 37, without damaging the conduit wall, the conduit (including sacrificial layer) is placed overtop the shaft as shown in FIG. 13. An end of the conduit is slid over the shoulder portion 41 of the shaft 39 forming an adequate seal. The other end of the conduit is pulled back in an axial direction so that the conduit is contracted as shown in region 42, exposing and separating the end portion of sacrificial layer 17 from the conduit. Vacuum source 38 applied to the inner space of the shaft, leads to a pressure differential between the inside and the outside of the inner layer where it has separated from the conduit. This urges the inner layer onto the shaft, and into the slot, and the separation propagates along the length of the section of conduit, sucking the sacrificial layer from the inner wall of the conduit 37. The portion of sacrificial layer 17 immediately opposite slot 40 is sucked so that it protrudes into the shaft interior. It may be necessary to initiate this release process at the exposed end (free end of the shaft) of the sacrificial layer 17 by hand (by bringing the separated end portion of the inner layer adjacent the slot. Helical reinforcing bead 43 prevents the conduit itself from being drawn into slot 40). After release of the sacrificial layer from the inner wall of the conduit 37, the conduit can be easily removed by sliding it off the shaft. Removal of the vacuum from the shaft allows removal of the remaining sacrificial layer more easily.

Applying the molten bead between the overlapping layers of tape instead of over the top of the overlapping layers may improve the weld quality, as both layers of tape that are to be welded are in physical contact with the molten bead. This lay-up may also reduce overheating problems by lowering the temperature necessary to properly bond the molten bead. When the prior art forming method shown in FIG. 1 is employed to manufacture conduits from very thin film or ribbon, (for example, having a wall thickness less than approximately 50 microns), consistently producing a high quality surface within the conduit has been found to be problematic.

Figure 11:
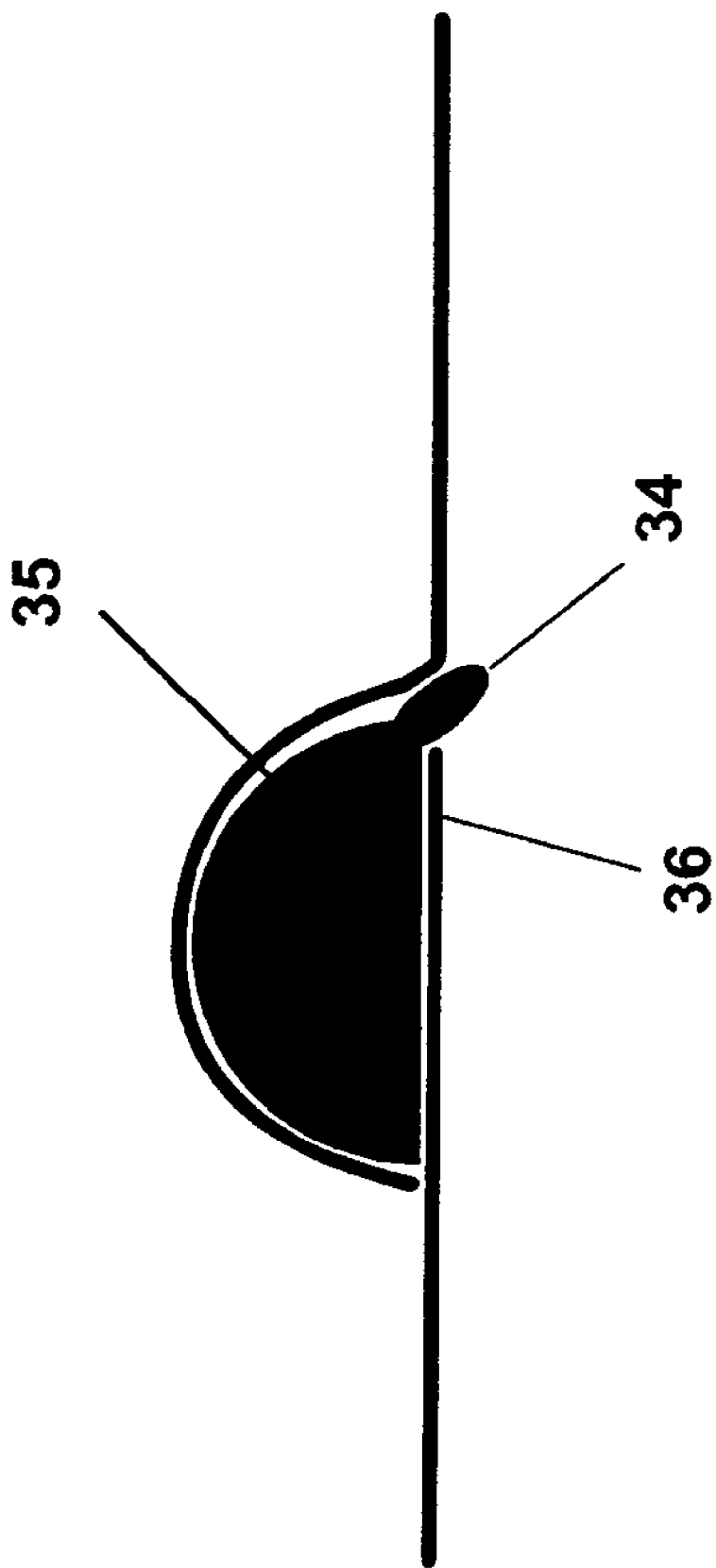
FIG. 11 is a cross sectional elevation of a conduit wall showing a defect caused by the bead flowing between overlapping adjacent layers.

FIG. 4 and FIG. 11 illustrates some potential problems which may occur during the production of conduit resulting in inferior wall smoothness. The quality of the surface finish for the inner surface of a breathing conduit is important, because rough inner surfaces may hinder gases flow and may cause more condensation to build up in the conduit. A protruding or flapping portion 33 may result if the underlapping layer of film is not completely bonded to the molten bead. This problem may occur if the underlapping portion of film is too wide or positioned on the former incorrectly. Similarly, overflow of molten bead 35, may result in a protrusion or defect 34, if the underlapping portion 36 of the underlapping layer does not extend far enough under the bead. Small voids 9 or undulations, may result between adjacent strips of ribbon if the film does not closely conform to the contour of the molten bead. This may occur if the thin ribbon is not sufficiently supple. For this reason the construction technique of the present invention is especially suited to conduits fabricated from thin supple film. The thin film is highly flexible and able to conform closely to the shape of the raised rib of the applied molten bead 8 during fabrication. By lapping very closely on to the bead and wrapping around the bead, the thin film maintains a smooth inner surface on the finished conduit product. A further defect 44, is shown where the overlapping portion of the layer overlaps the bead too much. The molten bead will also flow to fill voids or undulations between the lay-up, resulting in a smooth conduit wall. It will be appreciated that the conduit wall cross section shown in FIG. 2 and FIG. 11 is illustrative and not meant to be interpreted strictly in regard to the space shown between the bead and the conduit wall layers. The application of a sacrificial layer onto the former before the conduit wall is formed, is especially suited to the conduit forming method wherein the molten bead is applied between overlapping layers. The presence of the sacrificial layer ensures that the helically arranged rotating rods on the former do not become fouled with molten polymer.

Throughout the diagrams, the helical reinforcing bead is shown as having a substantially semi-circular cross section. It is however envisaged that the actual cross sectional shape of the reinforcing bead may vary. For example the presence and thickness of the film which overlaps the reinforcing bead, may affect the shape of the reinforcing bead by flattening the bead, resulting in a less rounded and more square or rectangular cross section. Further, rollers may be employed to shape the bead. The semi-circular reinforcing bead shown in the accompanying drawings is purely illustrative and not intended to be in any way limiting.

It has been found that breathing conduits formed according to the first preferred embodiment described above are extremely light, flexible and provide good crush resistance. However conduits having very thin walls may have a reduced resistance to axial deformation and/or stretching. Due to the thin tape used to form the walls of the conduit, the resulting product may be prone to expansion and/or contraction along the axis of the conduit. In use axial forces arising from patient breathing are capable of producing axial extension/contraction along the length of the conduit. In order to improve the axial stiffness of such breathing conduits, a further embodiment will now be described.

In a further embodiment shown in FIG. 5 a plurality of reinforcing threads 10, running the length of the wall and spaced around the perimeter of the tube are aligned parallel to one another and substantially parallel to the major axis of the conduit. The threads 10 are supported by the helical bead 11, with the threads spanning the spaces between turns of the helical bead. In this embodiment it is may be desirable to choose the reinforcing threads (material, gauge, type and number) such that the threads are sufficiently stiff to improve the conduits ability to resist buckling under the transiently reduced internal pressures that could be expected during patient breathing. Unrestrained or excessive buckling of the threads may result in unacceptable levels of conduit axial contraction and/or extension. The axial threads 10 may be spun or braided fibres or drawn or extruded mono filaments or other equivalent forms. Tensile reinforcement may be provided by braided or spun fibres while compressive and/or flexural reinforcement may be provided by drawn or extruded mono filaments.

Figure 6:
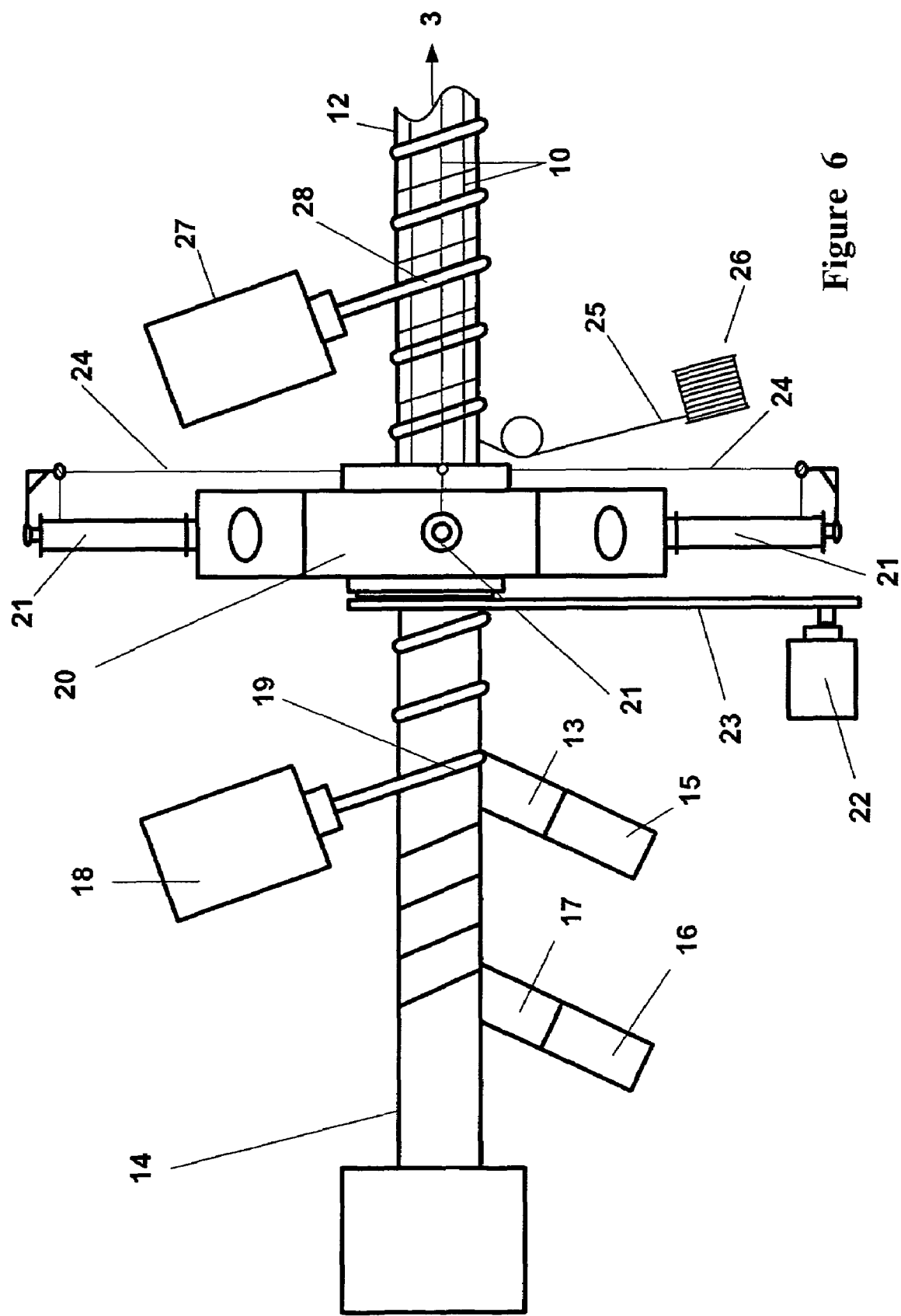
FIG. 6 is a plan view of a conduit forming device for forming a reinforced conduit according to an embodiment of the present invention, such as the conduit pictured in FIG. 5.

A method of forming the tube according to the embodiment of FIG. 5 is described with reference to the apparatus shown in FIG. 6. In particular in the machine of FIG. 6 the tube 12 is formed by helically wrapping a preformed tape or strip of polymer 13 on to a rotating former 14. The strip 13 unrolls from reel 15. In an analogous manner to that described previously for the first preferred embodiment, a sacrificial layer of polypropylene 17, is wound in an overlapping helix onto former 14 from spool 16. The sacrificial layer 17, between the mandrel and the conduit being formed, allows the extremely thin film to be shielded from the mandrel and higher operating temperatures.

Tube being formed on the former is rotated and advanced in the direction of arrow 3. The advance speed of the former is selected relative to the rotational speed so that the pitch of the helical laying of the strip or tape on to the former 14, is a little less than the width of the strip so that adjacent turns narrowly overlap. An extruder 18 extrudes a bead 19 of molten polymer material. The molten bead 19 deposits between the overlapping portions of adjacent winds of tape 13 and is sufficiently molten to weld to the strips of tape 13. The molten bead becomes the helical reinforcement for the finished conduit.

A freely rotatable thread laying head 20 is located over the former after the bead extruder 18. The rotating head 20 carries a plurality of spools 21 holding reinforcing thread. The head 20 is rotatable by an electric motor and drive belt 22 and 23 respectively. The head 20 is preferably rotated at a speed synchronized with the speed of effective rotation of the product 12. Advancement of tube along the former 14 draws thread 24 from the spools 21 to be laid as parallel threads 10 on the outside of the reinforcing bead 19. Another thread 25 is drawn from spool 26 and wound onto the former overtop of the longitudinal threads 10, laid by thread laying head 20. The thread 25 is laid on the former in a helical pattern such that the thread lies between the helical bead of molten polymer extruded from extruder 18. The purpose of thread 25 is to provide a temporary means of securing the plurality of longitudinal threads in position in preparation for permanent fixing. A second extruder 27 extrudes a second bead of molten polymer material 28 and deposits it over top the plurality of reinforcing threads 10 and directly on top of the first reinforcing bead 19 and bonds. The second bead of molten polymer sandwiches the plurality of longitudinal threads between itself and the first reinforcing rib formed by polymer bead 19. Thread 25 however, lies between these overlapping reinforcing beads and does not become permanently bonded to the conduit wall, allowing it to be removed. Thread 25, may be discarded or drawn from the former in a position subsequent to the application of the second reinforcing bead 28 and wound onto a spool for re-use.

This embodiment of the invention provides a breathing circuit limb reinforced against crushing by the helical bead and against longitudinal extension by the axial threads 10 as well as providing a breathing conduit having all the advantages of the first preferred embodiment. The spanning threads 10 also provide an additional advantage by reducing direct contact between the user/environment and the surface of the tube, therefore reducing the risk of punctures and damage. The threads effectively provide an additional barrier against potential damage around the conduit wall. It will be appreciated that the foregoing method of reinforcing a conduit is not limited to conduits wherein the helical reinforcing bead is interposed between the overlapping layers.

A further breathing circuit component to which the present invention may be applied is catheter mounts. A catheter mount connects between a patient interfacing component such as a mouth piece, nasal mask or endotracheal tube and the dual limbs of the breathing circuit. Connection with the dual limbs of the breathing circuit is generally via a wye connector. The extreme flexibility of very thin walled tubes manufactured according to the methods herein, makes them particularly useful in a catheter mount component.

It should be appreciated that with all of the forming methods described involving winding of a narrow ribbon or strip to create a tube, it would be possible to wind two or more ribbons or films simultaneously onto the former so that the turns created by each ribbon are interposed by turns of other ribbons, edges overlapping and being bonded together by an interposed extruded helical rib. For example a pair of ribbons may be laid as a double helix. This would require a multiplication in the number of forming stations associated with the wound on components of the tube or conduit. Further it is envisaged that for methods where a preformed tape is supplied to a former, the tape may be provided as a laminate having a thin film layer and a reinforcing layer bonded to it. Where the thin film layer is a breathable layer, the reinforcing layer is also permeable and allows the passage of water vapour.

Figure 7:
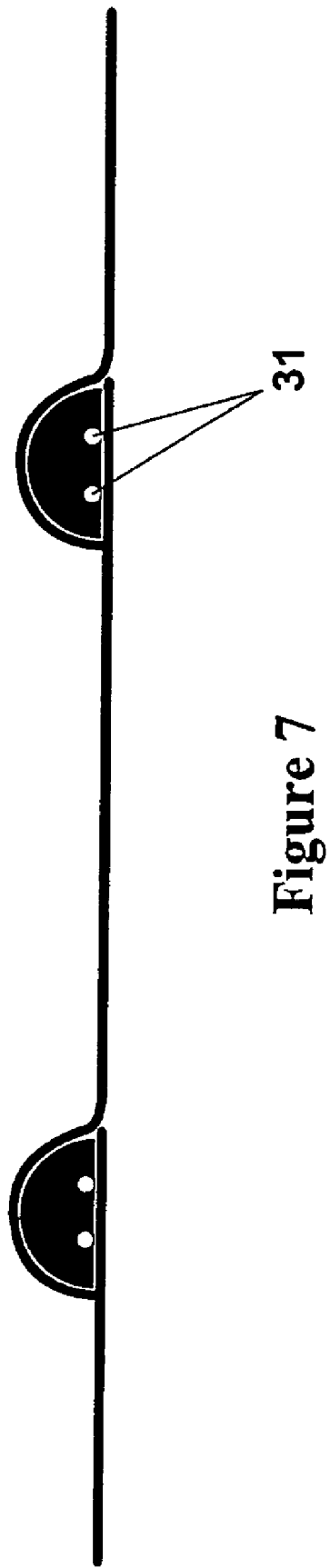
FIG. 7 is a cross sectional side elevation of a conduit wall according to a further embodiment of the present invention including a pair of heater wires within the conduit wall.

A further embodiment of the present invention is envisaged where thin walled breathing conduits are manufactured in a similar manner as described above but, where the conduit wall also preferably contains at least one thin conductive wire. A pair of wires may be included in order to provide a means for heating the conduit and or to carry electrical signals to sensors or transducers. Heated conduits may reduce the build up of condensation in the conduit and may also offer a means to maintaining the temperature of humidified gases flowing through the conduit. Heated conduits are most often used in only the inspiratory arm of a breathing circuit but can also be used in the expiratory arm. Heated wall conduits may also be components of coaxial (unilimb) circuits, or be used in single limb applications such as for CPAP therapy. In such breathing conduits where the inspiratory arm includes heater wires, the corresponding connectors at at least one end of the conduit will include an electrical connection suitable for connection with the humidified gases source in order to supply electrical energy to the conduit heater wires. Referring to FIG. 7, a breathing conduit is shown including a pair of heater wires 31, embedded in the helical reinforcing bead.

Figure 8:
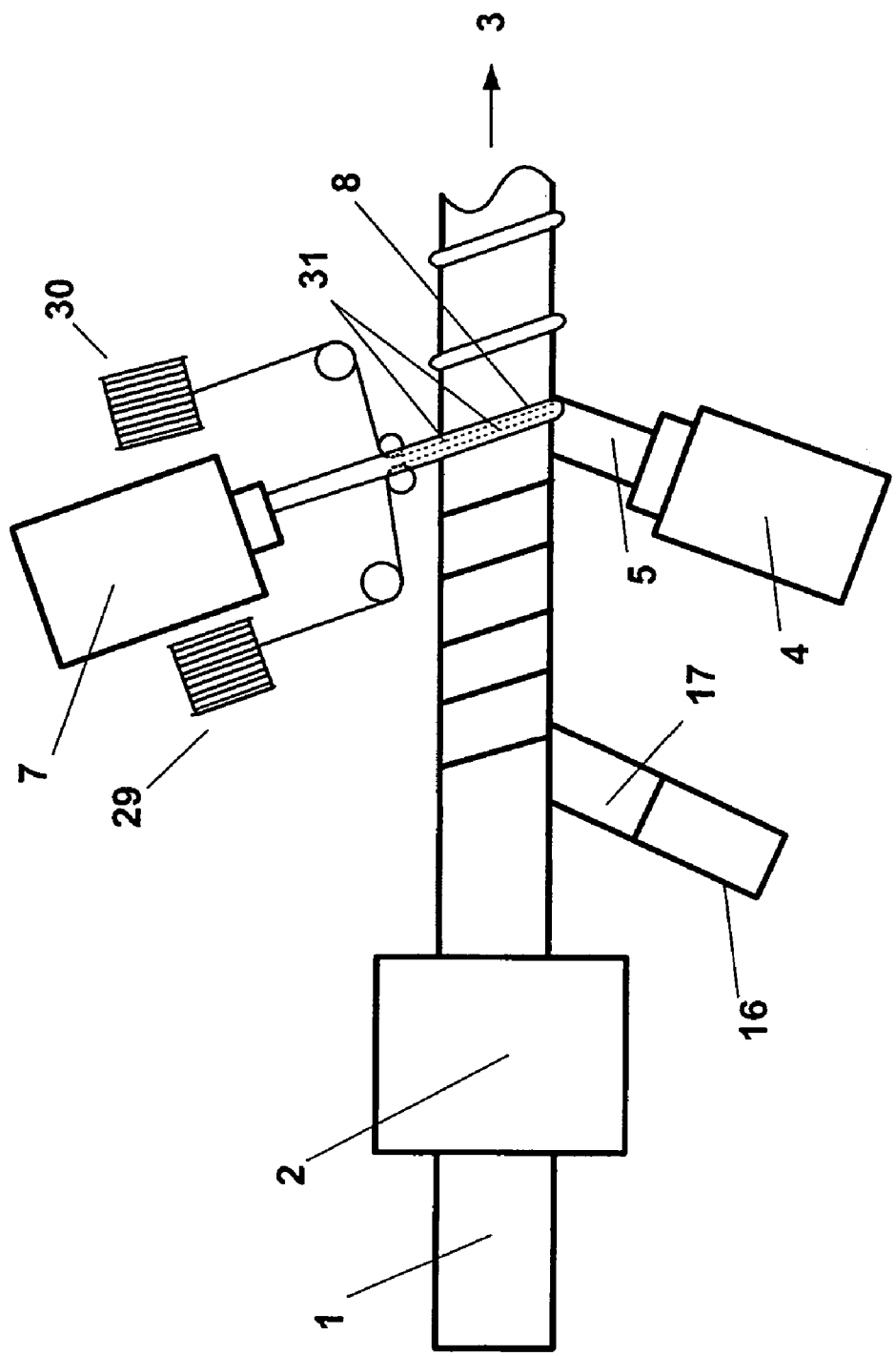
FIG. 8 is a plan view of a conduit forming device for forming the conduit pictured in FIG. 7.

A method of forming a conduit according to this embodiment of the present invention including a pair of heater wires will now be described with reference to FIG. 8. The method is similar to the method previously described and illustrated in FIG. 3, but an additional stage is required to lay a pair of parallel wires in between the overlapping adjacent winds of film in the edge area of the film that will become the seam. A pair of wires 31 are supplied from two reels 29 and 30. The wires are laid on top of the first wind of film, towards the edge, after it is laid on the former but before the molten bead is applied. FIG. 8 shows a pair of heater wires 31 in hidden detail under the molten bead 8. The molten bead 8 is then laid over the wires on top of the first layer of film before the following overlapping wind of film wraps around the former and completes the tube. It will be appreciated that each of the film, heating wire(s), and reinforcing bead may be applied in a different plane in order to achieve the desired spatial lay-up.

The resulting conduit is shown in FIG. 7 and is similar to the previous embodiment shown in FIG. 2, but includes an additional pair of heater wires embedded in the helical reinforcing bead of the conduit wall. In this embodiment, a sacrificial layer 17 may also be wound in an overlapping helix onto the former from spool 16. The sacrificial layer 17 may be a polypropylene layer or some other material that will not weld to the conduit wall. The sacrificial layer 17 between the mandrel and the conduit being formed, allows the extremely thin film to be shielded from the higher operating temperature of the mandrel and alleviates overheating of the film.

A further method of forming a conduit according to the present invention including a pair of heater wires will now be described.

The above method of forming a conduit discloses an online process for winding a pair of heater wires into the conduit wall. It is envisaged that a pair of heater wires may be included in a preformed tape which would then be used to form the walls of the conduit in a similar method to that described above and illustrated in FIG. 3. FIGS. 9a and 9b show cross sections of such a tape being formed by laying a pair of parallel wires a distance x from one edge of the tape. The length x of tape between the wires and the edge is then folded over and back onto the rest of the tape so as to enclose the pair of parallel wires, as shown by arrow 32. A secondary thermal welding process may then be employed to bond the folded portion of tape so as to permanently embed the parallel wires. It will be appreciated however that a secondary thermal welding process may not be necessary if the extruded tape is molten or semi-molten when the folding occurs. In this case the two regions of molten layer, when folded and pressed together will bond.

Such a pre-formed folded tape including embedded wires may then be wound on to reels and supplied to a conduit forming process such as that described previously and illustrated in FIG. 3 to produce a breathing conduit with a pair of integral heating wires. FIG. 10 shows the lay-up of a breathing conduit formed by this embodiment of the present invention. The portion of thin film that wraps over the reinforcing bead and the adjacent wind on the former is only one layer thick and therefore is able to conform to the contour of the reinforcing bead. A tube formed according to this embodiment of the present invention therefore is able to retain all of the advantages of the previously described preferred embodiments, while having the additional advantage that a forming apparatus as described in FIG. 3 may be employed to manufacture a conduit including embedded heater wires without substantial modification to the forming apparatus. In such a case the extruder 4 is replaced with a reel of pre-formed folded tape such as that shown in FIG. 9b and supplied to the forming apparatus.

The invention claimed is:

1. A method for removing a releasable inner layer from within a conduit comprising:
    placing said conduit, including said inner layer around an elongate shaft having a longitudinal slot,
    forming an adequate seal toward a first end of said shaft, effective for the conduit to at least substantially seal said slot, from the surroundings, apart from at the other end of said shaft,
    applying suction to said slot,
    initiating release of said inner layer from said conduit,
    removing said conduit from said shaft after said inner layer is released from said conduit.

2. A method for removing a releasable inner layer from within a conduit as claimed in claim 1, wherein said step of initiating includes urging said inner layer at a position toward said other end of said shaft, into said slot, said urging forming an adequate seal between said shaft and said layer.

3. An apparatus for assisting removal of a releasable inner layer within a conduit comprising:
    an elongate shaft having a longitudinal slot,
    a effective sealing means for making an adequate seal between said inner layer and said shaft, toward a first end of said shaft,
    a means to suck gases from said slot, and release said inner layer from said conduit.

* * * * *